US008710255B2

(12) United States Patent
Gao et al.

(10) Patent No.: US 8,710,255 B2
(45) Date of Patent: Apr. 29, 2014

(54) SITAGLIPTIN INTERMEDIATE COMPOUNDS, PREPARATION METHODS AND USES THEREOF

(75) Inventors: Hongjun Gao, Taizhou (CN); Min Li, Taizhou (CN)

(73) Assignee: Zhejiang Jiuzhou Pharmaceutical Co., Ltd., Taizhou (CN)

( * ) Notice: Subject to any disclaimer, the term of this patent is extended or adjusted under 35 U.S.C. 154(b) by 32 days.

(21) Appl. No.: 13/636,486

(22) PCT Filed: Mar. 22, 2011

(86) PCT No.: PCT/CN2011/072050
§ 371 (c)(1),
(2), (4) Date: Sep. 21, 2012

(87) PCT Pub. No.: WO2011/116686
PCT Pub. Date: Sep. 29, 2011

(65) Prior Publication Data
US 2013/0012735 A1    Jan. 10, 2013

(30) Foreign Application Priority Data
Mar. 25, 2010 (CN) .......................... 2010 1 0135469

(51) Int. Cl.
C07C 69/96   (2006.01)
C07C 68/06   (2006.01)
C07C 229/34  (2006.01)

(52) U.S. Cl.
CPC ............... C07C 68/06 (2013.01); C07C 68/065 (2013.01); C07C 69/96 (2013.01); C07C 229/34 (2013.01)
USPC ........................................... 558/275; 560/42

(58) Field of Classification Search
None
See application file for complete search history.

(56) References Cited

U.S. PATENT DOCUMENTS

2009/0123983 A1   5/2009   Niddam-Hildesheim
2009/0192326 A1   7/2009   Perlman et al.

OTHER PUBLICATIONS

International Search Report dated Jun. 23, 2011, from related International Patent Application No. PCT/CN2011/072050, with English translation (6 pages).
Sun, Guifang, et al., "Graphical Synthetic Routes of Sitagliptin"; Chinese Journal of Pharmaceuticals, vol. 39, No. 5, 2008; pp. 383-386.

Primary Examiner — Alicia L Otton
(74) Attorney, Agent, or Firm — Osha Liang LLP

(57) ABSTRACT

Sitagliptin intermediate compounds of formula (f) and methods of preparation and use thereof are disclosed. Compounds of formula (f) are prepared by the following steps: compounds of formula (a) are subjected to electrophilic reaction with benzyl halides to form compounds of formula (b), which then react with compounds of formula (i) to form novel compounds of formula (e). Gignard agents formed from 2,4,5-trifluoro bromobenzene and magnesium metal react with compounds of formula (e) to afford compounds of formula (f), which are novel intermediates for the preparation of Sitagliptin intermediates of formula (g). Compounds of formula (f) are subjected to reduction by Pd/C, debenzylation, substitution of protecting group to form compounds of formula (g). Compounds of formula (a), (b), (i), (e), (f), and (g) have the following structures, in which R is protecting group of carboxyl and $R^2$ is (substituted) hydrocarbyl.

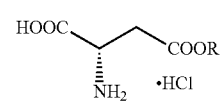

a

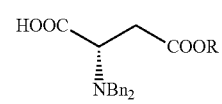
b

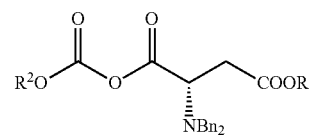
e

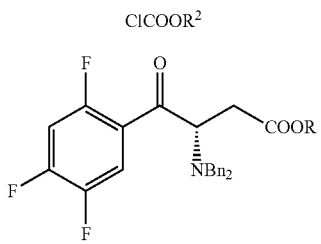
i f

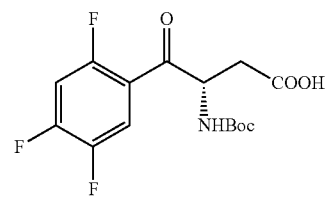
g

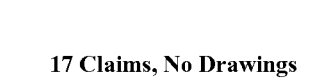

17 Claims, No Drawings

SITAGLIPTIN INTERMEDIATE COMPOUNDS, PREPARATION METHODS AND USES THEREOF

CROSS REFERENCE TO RELATED APPLICATIONS

This application is a national stage application based on PCT/CN2011/072050, filed on Mar. 22, 2011, which claims the priority to Chinese Patent Application No. 201010135469.8, filed with the Chinese State Intellectual Property Office on Mar. 25, 2010, and entitled "SITAGLIPTIN INTERMEDIATE COMPOUNDS, PREPARATION METHODS AND USES THEREOF," which is incorporated herein by reference in its entirety.

FIELD OF THE INVENTION

The present invention relates to pharmaceutical intermediate compounds, in particular, to the intermediate compounds of Sitagliptin, preparation methods and uses thereof.

BACKGROUND OF THE INVENTION

Sitagliptin n has a chemical name of (2R)-4-oxo-4-(3-(trifluoromethyl)-5,6-dihydro(1,2,4)triazolo[4,3-a]pyrazin-7(8H)-yl)-1-(2,4,5-trifluorophenyl)butan-2-amine, hydrochloride form of which has a structural formula shown as follows:

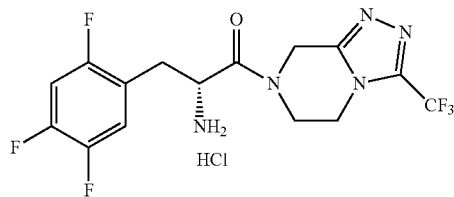

Sitagliptin is the first agent in the class of Dipeptidyl Peptidase-IV (DPP-IV) inhibitors developed by Merck America. In October 2006, Sitagliptin phosphate became the first Dipeptidyl Peptidase-VI (DPP-VI) inhibitor to gain FDA approval for clinical use in the treatment of type 2 diabetes. This medication has the advantages of fewer adverse effects, a lower risk of hypoglycemia, and no weight gain (body-weight neutrality).

The current preparation methods of Sitagliptin intermediate compounds are disclosed in the following references:

Reference 1: Journal of Medicinal Chemistry (J. Med. Chem.), 2005, Vol. 48, No. 11, page 141-151, by Kim D et al. The scheme disclosed is depicted below:

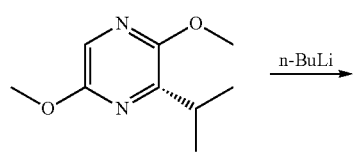

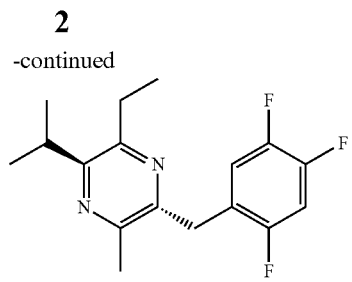

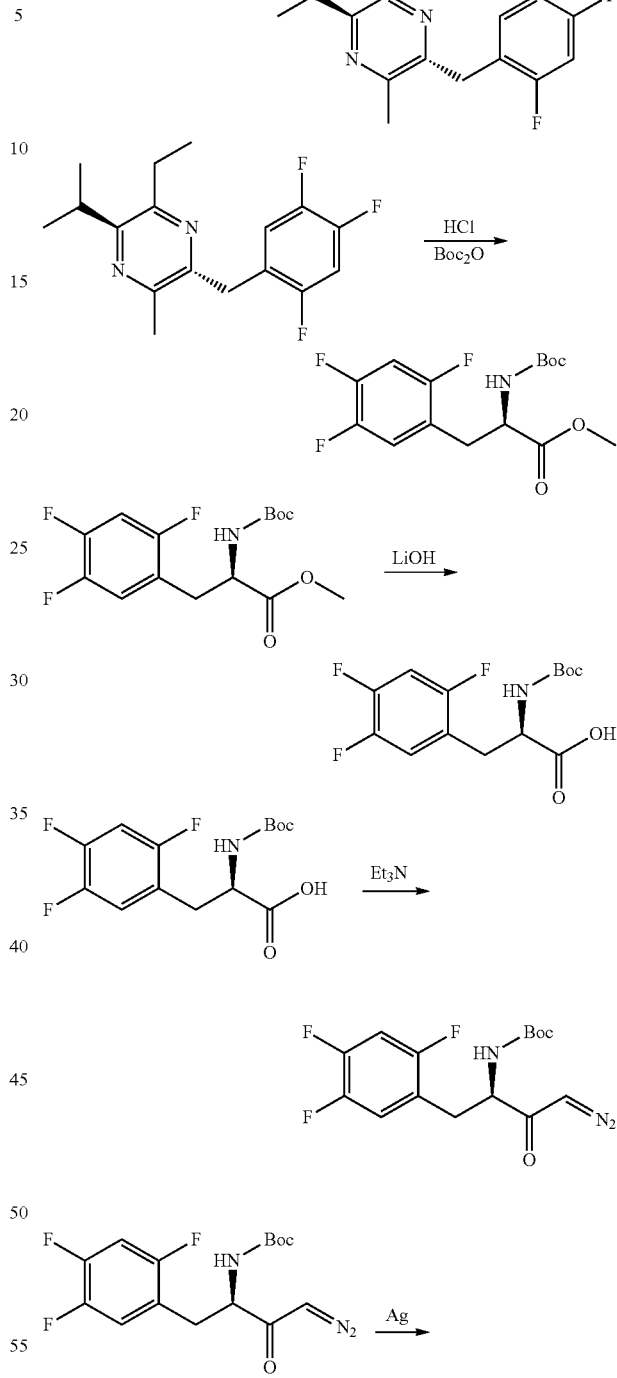

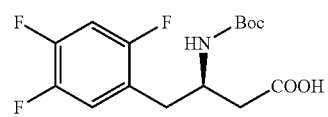

Reference 2: Org. Proc. Res. Dev, 2005, 9(5): 634-639, by Hansen K B, Balsells J, et al. The scheme disclosed is depicted below:

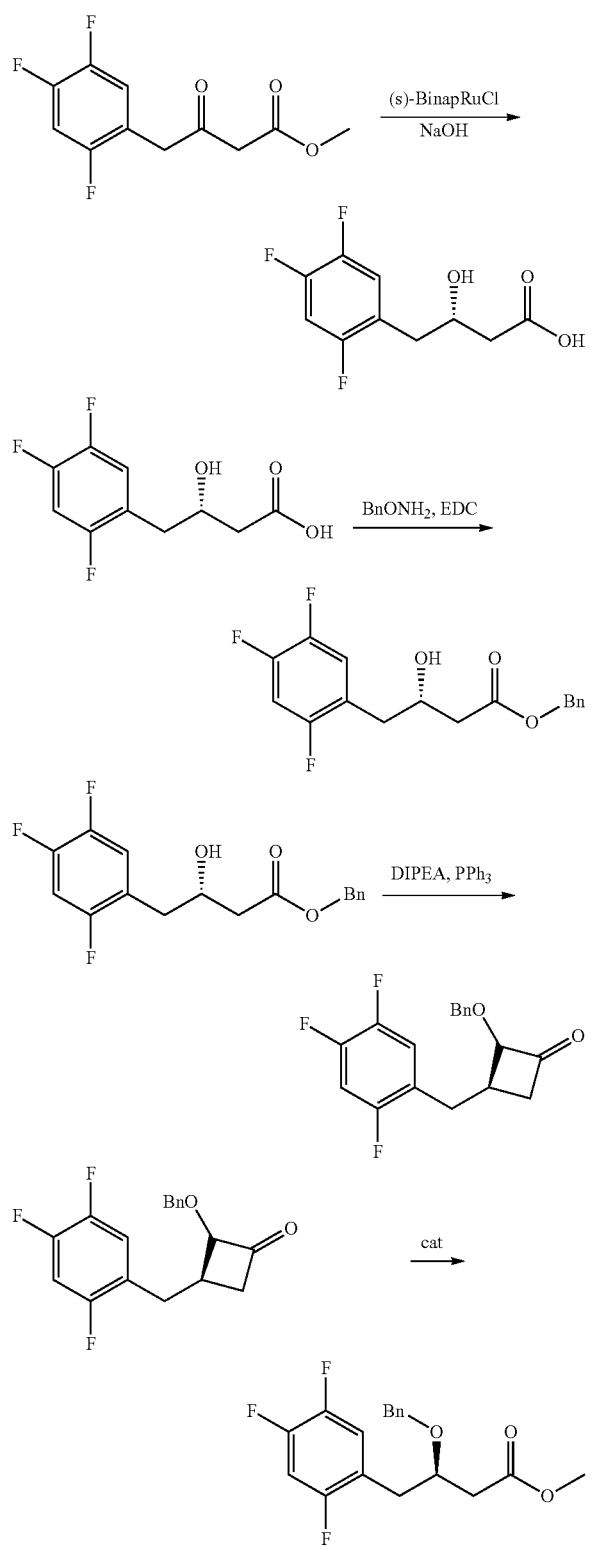

From the above references, it is clear that they have common disadvantages of expensive starting materials, complexity of the reactions, long synthetic routes, strict operating conditions, low yields, difficulty in optimize the production, and being unable to carry out large scale production, which limit the wide application of Sitagliptin.

SUMMARY OF THE INVENTION

A first object of the invention is to provide novel intermediate compounds of formula (f) for use in the preparation of Sitagliptin:

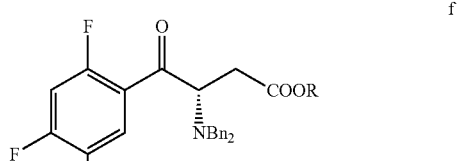

wherein R is a carboxyl protecting group.

In preferred compounds of formula (f) provided in the invention, R is $C_1$~$C_8$ chain alkyl or cycloalkyl, phenyl or substituted phenyl, benzyl or substituted benzyl.

In further preferred compounds of formula (f) provided in the invention, R is methyl, ethyl, propyl, isopropyl, butyl, isobutyl, tert-butyl, cyclopropyl, cyclopentyl, cyclohexyl, p-chlorophenyl, phenyl, p-chlorobezyl, or benzyl.

A second object of the invention is to provide other intermediate compounds of formula (e) for use in the preparation of compounds of formula (f):

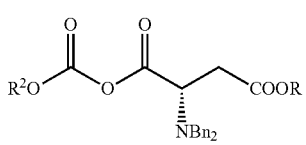

wherein R has the same meanings defined above for the compounds of formula (f), $R^2$ is hydrocarbyl or substituted hydrocarbyl.

In preferred compounds of formula (e) provided in the invention, R is $C_1$~$C_8$ chain alkyl or cycloalkyl, phenyl or substituted phenyl, benzyl or substituted benzyl; $R^2$ is chain alkyl or chain substituted alkyl, cycloalkyl or substituted cycloalkyl, alkenyl or substituted alkenyl, phenyl or substituted phenyl, benzyl or substituted benzyl.

In further preferred compounds of the formula (e) provided in the invention, R is methyl, ethyl, propyl, isopropyl, butyl, isobutyl, tert-butyl, cyclopropyl, cyclopentyl, cyclohexyl, p-chlorophenyl, phenyl, p-chlorobezyl, or benzyl; $R^2$ is methyl, ethyl, propyl, isopropyl, butyl, isobutyl, tert-butyl, trichloroethyl, 2-chloropropyl, cyclopropyl, cyclopentyl, cyclohexyl, 3-bromocyclohexyl, ethenyl, propenyl, phenyl, p-nitrophenyl, p-chlorophenyl, benzyl, p-nitrobenzyl, or p-chlorobenzyl.

A third object of the invention is to provide processes for preparation of compounds of formula (e), as indicated in the following chemical scheme:

Step A:

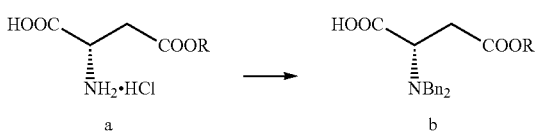

Step B:

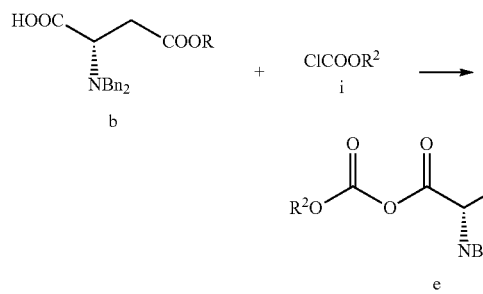

wherein R and $R^2$ have the same meanings defined above for the compounds of formula (e) and (f).

Specific embodiments are as follows:

Step A: Compounds of formula (a) are dissolved in an organic solvent and, in the presence of a base, reacted with a benzyl halide to undergo N-substitution reactions. After the completion of a reaction, the reaction solution is neutralized with an acid to produce a neutralized solution. After concentration of the solution under vacuum, followed by separation and washing, a crude product is obtained.

In this reaction, the benzyl halide is benzyl chloride or benzyl bromide, and the molar ratio of the benzyl halide to the compound of formula (a) is (2~5) to 1. The organic solvent is selected from alkanols, preferably methanol, ethanol, isopropanol, n-propanol or n-butanol; the amount of the solvent is 5~100 times that of the compound, preferably 20~50 times. The base may be triethylamine, pyridine, sodium carbonate, sodium bicarbonate, potassium carbonate, potassium bicarbonate; the molar ratio of the base to the compound is (2~10) to 1. The acid is hydrochloric or citric acid. The reaction temperature is 0~45° C., preferably 15~30° C. The reaction times are 4~36 h.

Step B: under an atmosphere of nitrogen, a compound of formula (b) is reacted with a compound of formula (i) in the presence of a base to undergo substitution reactions. After the completion of the reaction, a product is obtained, which may be used without further purification.

The base used in the reaction may be triethylamine, pyridine, sodium carbonate, potassium carbonate, N,N-Diisopropylethylamine; the reaction solvent is selected from ethers, (substituted) benzenes, or alkane, wherein, preferred ethers solvent may be methyl-tert-butyl ether, tetrahydrofuran, methyltetrahydrofuran. The amount of the solvent is 1~100 times that of the compound of formula (b), preferably 20~50 times. Preferred (substituted) benzenes are benzene, methylbenzene (toluene), chlorobenzene, and preferred alkane is n-hexane. The reaction temperature is 0~45° C., preferably 15~30° C. The molar ratio of the compound of formula (b) to the compound of formula (i) is 1 to (1~3). The molar ratio of the base to the compound of formula (b) is (1~2) to 1.

A fourth object of the invention is to provide processes for preparation of compounds of formula (f), as indicated in the following chemical reaction scheme:

Step C:

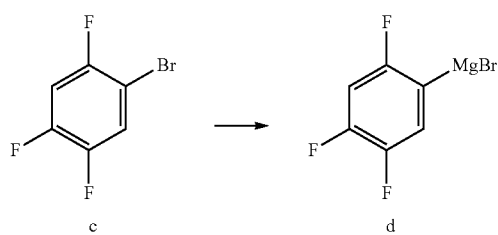

Step D:

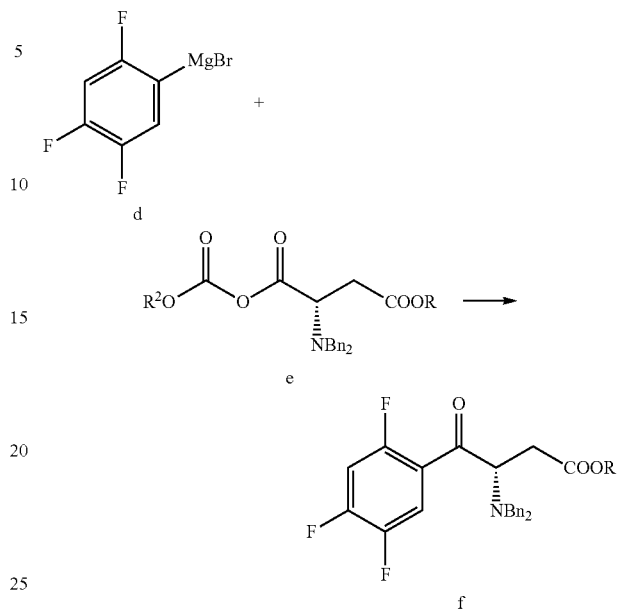

Specific embodiments are as follows:

Step C: In the presence of an initiator, a compound of formula (c) is reacted with magnesium or zinc metal in an organic solvent to obtain a Grignard reagent.

The initiator is iodine, iodoalkane, bromoalkane, Grignard reagent from a previous batch, or a mixture of one or more thereof. The iodoalkane includes, for example, iodomethane. The bromoalkane includes, for example, bromoethane and dibromoethane. For a liquid initiator, the amount of the initiator used is 1~2 weight % based on solvent used. For solid iodine, the amount of the initiator used is 0.1~0.2 weight % based on the solvent used. As appreciated by those skilled in the art, the reaction may be performed without adding an initiator under continuous operation. The organic solvents are ethers, (substituted) benzene solvents or mixtures thereof. The ether solvents includes, for example, ethyl ether, isopropyl ether, methyl tert-butyl ether, butyl ether, tetrahydrofuran, methyltetrahydrofuran, or a mixture of one or more thereof. Embodiments of the (substituted) benzene solvents includes, for example, toluene, benzene, chlorobenzene, or a mixture of one or more thereof. The amount of the solvent is 5~50 times that of the compound of formula (c), preferably 10~25 times. The molar ratio of the compound of formula (c) to magnesium or zinc metal is 1 to (1~12), preferably 1 to (1~5). The reaction temperature is −20~45° C., preferably 0~25° C., and the reaction times are 0.5~18 h, preferably 2~6 h.

Step D: A compound of formula (d) is reacted with a compound of formula (e). After completion of the reaction, the mixture is quenched with water, extracted, and concentrated to afford the product.

The molar ratio of the compound of the formula (e) to the compound of formula (d) is 1 to (1~5), preferably 1 to (1.01~2); the reaction temperature is −78~30° C., preferably −20~25° C. The reaction times are 0.5~10 h.

A fifth object of the invention is to provide one of the uses of the compounds of formula (f). A specific example is as follows:

A compound of formula (f) as starting material was used to prepare a compound of formula (h), which can be used for preparing a compound of formula (g) (an important intermediate for the preparation of Sitagliptin). Specific routes are depicted below:

Step E:

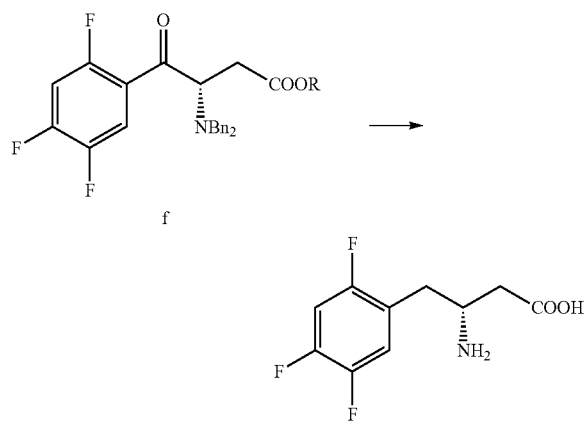

f h

Step F:

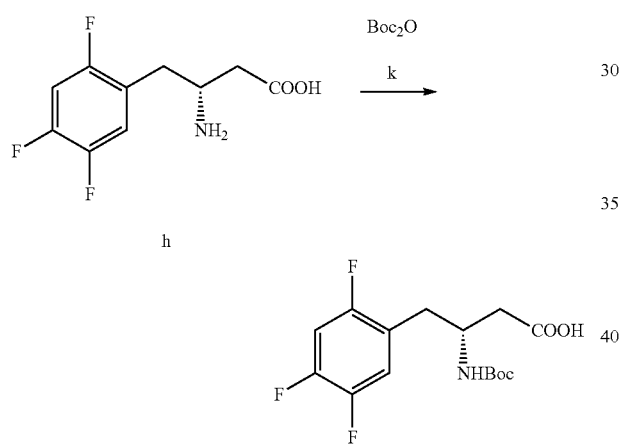

h g

Specific embodiments are as follows:

Step E:

In the presence of a catalyst, a compound of formula (f) is subjected to deprotection and carbonyl reduction. After completion of the reaction, the mixture was filtrated, concentrated, and converted to a salt to provide the product.

Wherein the catalyst is Pd/C or Raney Ni, preferably Pd/C. The molar ratio of the catalyst to the compound of formula (f) is (0.01~0.1) to 1. The reaction solvents are alkanols or ethers, or mixtures thereof. A preferred alkanol is methanol, ethanol, isopropanol, n-butanol or a mixtures of two or more thereof. A preferred ether is tetrahydrofuran or methyltetrahydrofuran. The amount of the solvent is 20~80 times that of the compound of formula (f), preferably 30~50 times. The reaction temperature is 0~65° C., preferably 15~45° C. The reaction times are 0.5~48 h, preferably 5~12 h. Hydrogen pressure is 0.1~10 Mpa; preferably 0.5~1.0 Mpa.

Step F: A compound of formula (h) is reacted with a compound of formula (k) in the presence of a base to undergo a substitution reaction. Then, by filtration, neutralization and concentration under vaccuo, an important intermediate of Sitagliptin is obtained.

Wherein the base is triethylamine, pyridine, sodium hydroxide, or potassium hydroxide. The molar ratio of the base to the compound of formula (h) is (1~15) to 1, preferably (1.5~5) to 1. The molar ratio of the compound of formula (h) to the compound of formula (k) is 1 to (1~5). The reaction solvent is tetrahydrofuran or dichloromethane, or a mixture thereof. The amount of the solvent is 15~100 times that of the compound of formula (h), preferably 30~50 times. The reaction temperature is 0~35° C., preferably 15~30° C.

A sixth object of the invention is to provide another one of the uses of the compound of formula (f) in the preparation of Sitagliptin. Such use is known in the art. Ffor example, the reaction may be performed by methods as described in Journal of Materials Chemistry (J Med Chem), 2005, volume 48, issue 11, page 141~151. Briefly, the reaction may be performed according to the following scheme:

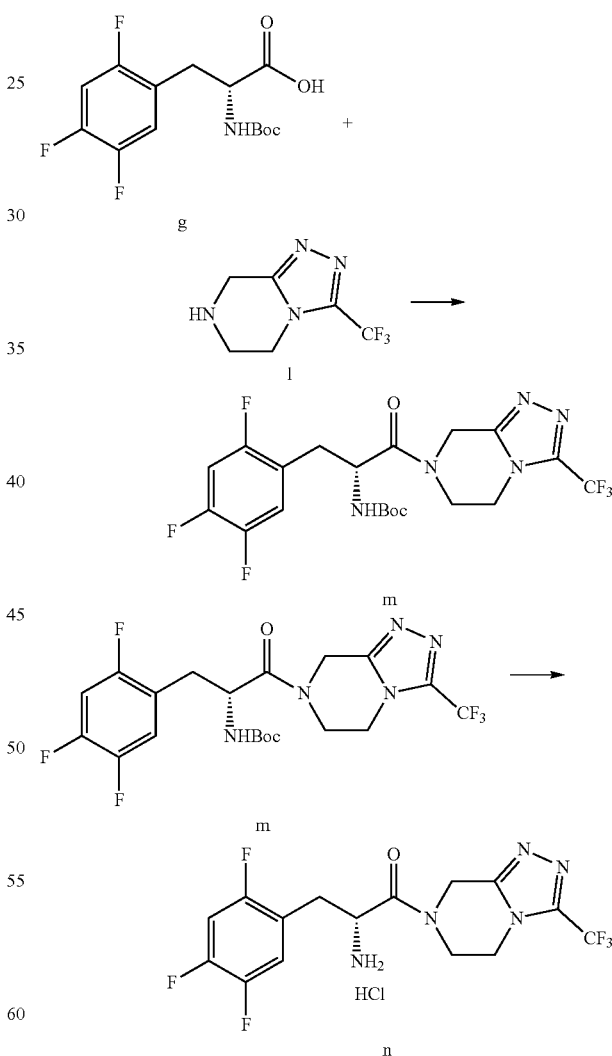

That is, a compound of formula (g) is subjected to a condensation reaction, in the presence of condensing agent, with a compound of formula (I) to afford a compound of formula (m). The compound (m) is subjected to deprotection and salification reaction with saturated hydrochloric acid methanol solution to form compound of formula (n), which is Sitagliptin hydrochloride form.

The invention possesses advantages in preparing Sitagliptin, such as, easily available starting materials, simple reaction types, mild reaction conditions, being suitable for industrial production, high yield, low cost, and providing two novel intermediate compounds. Accordingly, the invention possesses high values in commercial application and economy.

EXAMPLES

In order to further understand the invention, preferred embodiments of the invention now will be described in connect with examples. However, it should be understood that the descriptions herein are intended to illustrate the features and advantages of the invention, and not to limit the claims of the invention.

The invention will be illustrated in the following specific embodiments. However, the scope of protection of the present invention isn't limited by the following embodiments.

In order to better understand the invention, the invention will now be further illustrated by the following specific examples.

Step A:

Example 1

The Preparation of (S)-2-(dibenzylamino)-4-methoxy-4-oxobutanoic acid (R is methyl)

To a solution of 10 g (S)-2-amino-4-methoxy-4-oxobutanoic acid hydrochloride in 400 ml methanol was added 15 g sodium carbonate, and the mixture was stirred at 25° C. Twenty (20) g benzyl chloride was then added dropwise at this temperature. After completion of the reaction, the mixture was maintained at this temperature for 12 h. The reaction solution was neutralized with a diluted aqueous hydrochloride acid solution to produce a neutralized solution. Methanol was evaporated, and the residue was partitioned and extracted with ethyl acetate. The organic layer was concentrated and then washed with water 2~3 times to afford 16 g crude (S)-2-(benzylamino)-4-methoxy-4-oxobutanoic acid, with a yield of 91.3%.

Example 2

The preparation of (S)-4-(benzyloxy)-2-(dibenzylamino)-4-oxobutanoic acid (R is benzyl)

The procedure of example 1 was repeated by using 10 g (S)-2-amino-4-(benzyloxy)-4-oxobutanoic acid hydrochloride as a starting material to obtain 12.5 g (S)-4-(benzyloxy)-2-(dibenzylamino)-4-oxobutanoic acid, with a yield of 80.6%.

Example 3

The Preparation of (S)-4-(4-chlorophenoxy)-2-(dibenzylamino)-4-oxobutanoic acid (R is 4-chlorophenyl)

10 g (S)-2-amino-4-(4-chlorophenoxy)-4-oxobutanoic acid hydrochloride was subjected to the procedure described in example 1 to obtain 12.3 g (S)-4-(4-chlorophenoxy)-2-(dibenzylamino)-4-oxobutanoic acid, with a yield of 81.2%.

Example 4

The Preparation of (S)-4-(4-chlorobenzyloxy)-2-(dibenzylamino)-4-oxobutanoic acid (R is 4-chlorobenzyl)

10 g (S)-2-amino-4-(4-chlorobenzyloxy)-4-oxobutanoic acid hydrochloride was subjected to the procedure described in example 1, to obtain 12.25 g (S)-4-(4-chlorobenzyloxy)-2-(dibenzylamino)-4-oxobutanoic acid, with a yield of 82.3%.

Step B:

Example 5

The Preparation of (S)-2-(dibenzylamino)-4-methoxy-4-oxobutanoic(ethyl carbonic)anhydride (R is methyl, $R^2$ is ethyl)

Under a nitrogen atmosphere, to a solution of 10 g (S)-2-(dibenzylamino)-4-methoxy-4-oxobutanoic acid and 3.5 g triethylamine in 300 ml tetrahydrofuran was added dropwise 5.0 g ethyl carbonochloridate at 25° C., and the mixture was then maintained at this temperature for 2 h. After completion of the reaction, a solution of (S)-2-(dibenzylamino)-4-methoxy-4-oxobutanoic(ethyl carbonic)anhydride was obtained, the concentration of which is 0.1 mol/L. It was cooled to 0° C. and stored until needed.

Example 6

The Preparation of (S)-4-(benzyloxy)-2-(dibenzylamino)-4-oxobutanoic(methyl carbonic)anhydride (R is benzyl, $R^2$ is methyl)

10 g (S)-4-(benzyloxy)-2-(dibenzylamino)-4-oxobutanoic acid was subjected to the procedure described in example 5 to obtain a solution of (S)-4-(benzyloxy)-2-(dibenzylamino)-4-oxobutanoic(methyl carbonic)anhydride, the concentration of which is 0.08 mol/L.

Example 7

The Preparation of (S)-2-(dibenzylamino)-4-methoxy-4-oxobutanoic(methyl carbonic)anhydride (R is methyl, $R^2$ is methyl)

10 g (S)-2-(dibenzylamino)-4-methoxy-4-oxobutanoic acid was subjected to the procedure described in example 5, to obtain a solution of (S)-2-(dibenzylamino)-4-methoxy-4-oxobutanoic(methyl carbonic)anhydride, the concentration of which is 0.12 mol/L.

$^1$H NMR (500 MHz, CDCl$_3$) δ 2.72 (1H, dd, J=9.0, 20.0 Hz), 2.94 (1H, dd, J=9.0, 20.0 Hz), 3.65 (s, 3H), 3.75 (s, 4H), 4.00 (t, J=9.0 Hz), 7.26-7.30 (m, 2H), 7.30-7.36 (m, 8H); LRMS: 327.2 [M+].

Step C:

Example 8

The Preparation of (2,4,5-trifluorophenyl)-magnesium bromide

To magnesium spalls in a reaction flask, under an atmosphere of nitrogen, was added 50 ml tetrahydrofuran and 0.02 g iodine as an initiator. A solution of 9 g 1-bromo-2,4,5-trifluorobenzene in 150 ml tetrahydrofuran was added dropwise into the reaction system. The reaction was stirred at 25° C. for 3 h to obtain a solution of 0.21 mol/L (2,4,5-trifluorophenyl)-magnesium bromide.

Step D:

Example 9

The Preparation of (S)-methyl 3-(dibenzylamino)-4-oxo-4-(2,4,5-trifluorophenyl)butanoate (R is methyl, $R^2$ is ethyl)

To 100 ml of 0.1 mol/L (S)-2-(dibenzylamino)-4-methoxy-4-oxobutanoic(ethyl carbonic)anhydride solution in a reaction flask, under atmospheric nitrogen, was added dropwise 50 ml of 0.21 mol/L (2,4,5-trifluorophenyl)-magnesium bromide solution. The reaction was stirred at 25° C. for 2 h. After completion of the reaction, the reaction mixture was quenched with water, extracted with ethyl acetate. The aqueous layer is removed, and the organic layer was concentrated, to afford 3.8 g (S)-methyl 3-(dibenzylamino)-4-oxo-4-(2,4,5-trifluorophenyl)butanoate with a yield of 86.3%.

$^1$H NMR (500 MHz, DMSO) δ 2.89-2.99 (m, 2H), 3.52 (s, 4H), 3.61 (s, 6H), 4.45-4.47 (m, 1H), 7.06-7.08 (m, 4H), and 7.21-7.28 (m, 8H); LRMS: 441.1 [M+].

Example 10

The Preparation of (S)-benzyl 3-(dibenzylamino)-4-oxo-4-(2,4,5-trifluorophenyl)butanoate The procedure of example 9 was repeated by using 100 ml of 0.08 mol/L (S)-4-(benzyloxy)-2-(dibenzylamino)-4-oxobutanoic(methyl carbonic)anhydride solution as a starting material to obtain 3.4 g (S)-benzyl 3-(dibenzylamino)-4-oxo-4-(2,4,5-trifluorophenyl)butanoate with a yield of 82.1%.

Step E:

Example 11

The Preparation of (R)-3-amino-4-(2,4,5-trifluorophenyl)butanoic acid

To a solution of 3 g (S)-methyl 3-(dibenzylamino)-4-oxo-4-(2,4,5-trifluorophenyl)butanoate in 100 ml ethanol, was added 0.5 g of 10% Pd/C under an atmosphere of nitrogen. The atmosphere of nitrogen was replace with an atmosphere of hydrogen, and the reaction was carried out at 25° C. for 5 h. After completion of the reaction, the reaction mixture was filtered through diatomite. The filtrate was concentrated, and the pH was adjusted to 5~6 by addition of 10% hydrochloric acid. The aqueous layer was washed with ethyl acetate, and then concentrated to obtain 1.47 g (R)-3-amino-4-(2,4,5-trifluorophenyl)butanoic acid as white solid, with a yield of 93.2%.

Example 12

The Preparation of (R)-3-amino-4-(2,4,5-trifluorophenyl)butanoic acid

The procedure of example 11 was repeated using 4 g (S)-benzyl 3-(dibenzylamino)-4-oxo-4-(2,4,5-trifluorophenyebutanoate as a starting material to obtain 1.36 g (R)-3-amino-4-(2,4,5-trifluorophenyl)butanoic acid with a yield of 93.4%.

Step F:

Example 13

The Preparation of (R)-N-(tert-butoxycarbonyl)-3-amino-4-(2,4,5-trifluorophenyflbutanoic acid To a solution of 3 g (R)-3-amino-4-(2,4,5-trifluorophenyl)butanoic acid in 200 ml dichloromethane was added 3.5 di-t-butyl dicarbonate and 2 g triethylamine. The reaction was carried out at 20° C. for 10 h. After completion of the reaction, the solid was filtered off. The filtrate was neutralized with 10% diluted aqueous hydrochloride acid solution. The solution was concentrated, followed by purification by column chromatography. The column was eluted with ethyl acetate/n-hexane (1/2) to obtain 3.5 g (R)-N-(tert-butoxycarbonyl)-3-amino-4-(2,4,5-trifluorophenyl)butanoic acid, with a yield of 81.7%.

In conclusion, the invention relates to Sitagliptin intermediates, preparation methods and uses thereof. A compound of formula (e) was subjected to Grignard Reaction with a compounds of formula (d) that formed from a compounds of formula (c), to form a novel intermediate compound (f). From compounds (f), Sitagliptin intermediates of formula (g) can be prepared conveniently. The invention also provided processes for the preparation of novel compounds of formula (e). The compounds of formula (a) were subjected to electrophilic reactions with benzyl halides to form compounds of formula (b), which were then react with di-t-butyl dicarbonate to form novel compounds of formula (e).

All the documents mentioned in the present invention are incorporated herein by reference, as if each of them is individually incorporated. Further, it would be appreciated that the foregoing description presents specific embodiments and generic principles of the invention. Having read the above described teaching of the invention, one skilled in the art could make various changes or modifications to the invention without departing from the spirit and scope of the invention. These equivalents would still be within the scope of the invention.

The invention claimed is:

1. A compound of formula (f) having the following structure:

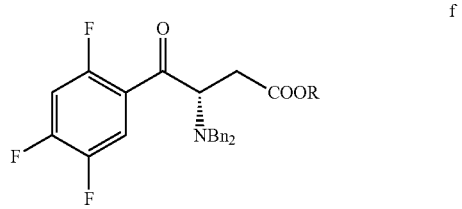

f wherein R is a protecting group of carboxyl.

2. The compound according to claim 1, wherein R is $C_1$~$C_8$ chain alkyl or cycloalkyl, phenyl, substituted phenyl, benzyl, or substituted benzyl.

3. The compound according to claim 2, wherein R is methyl, ethyl, propyl, isopropyl, butyl, isobutyl, tert-butyl, cyclopropyl, cyclopentyl, cyclohexyl, p-chlorophenyl, phenyl, p-chlorobezyl, or benzyl.

4. The compound according to claim 3, which is selected from the group consisting of:

(S)-methyl 3-(dibenzylamino)-4-oxo-4-(2,4, 5-trifluorophenyl)butanoate;

(S)-ethyl 3-(dibenzylamino)-4-oxo-4-(2,4,5-trifluorophenyl)butanoate; and (S)-benzyl 3-(dibenzylamino)-4-oxo-4-(2,4, 5-trifluorophenyl)butanoate.

5. A method for the preparation of the compound of formula (f) as defined in claim 1, comprising: reacting a Grignard reagent, formed from 2,4,5-trifluoro bromobenzene, with a compound of formula (e) to produce the compound of formula (f) by Grignard reaction,

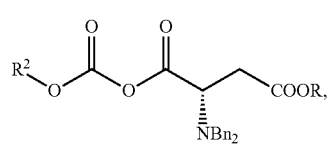

e wherein R is a protecting group of carboxyl, $R^2$ is hydrocarbyl or substituted hydrocarbyl.

6. The method according to claim 5, wherein $R^2$ is chain alkyl or substituted chain alkyl, cycloalkyl or substituted cycloalkyl, alkenyl or substituted alkenyl, phenyl or substituted phenyl, benzyl or substituted benzyl.

7. The method according to claim 6, wherein, $R^2$ is methyl, ethyl, propyl, isopropyl, butyl, isobutyl, tert-butyl, trichloroethyl, 2-chloropropyl, cyclopropyl, cyclopentyl, cyclohexyl, 3-bromocyclohexyl, ethenyl, propenyl, phenyl, p-nitrophenyl, p-chlorophenyl, benzyl, p-nitrobenzyl, or p-chlorobenzyl.

8. The method according to claim 7, the compounds of formula (e) is selected from the group consisting of:

(S)-2-(dibenzylamino)-4-methoxy-4-oxobutanoic (methyl carbonic) anhydride;

(S)-2-(dibenzylamino)-4-methoxy-4-oxobutanoic (ethyl carbonic) anhydride;

(S)-4-(benzyloxy)-2-(dibenzylamino)-4-oxobutanoic (methyl carbonic) anhydride; and (S)-4-(benzyloxy)-2-(dibenzylamino)-4-oxobutanoic (ethyl carbonic) anhydride.

9. The method according to claim 5, wherein the Grignard reagent is produced by reacting 2,4,5-trifluoro bromobenzene with magnesium or zinc metal to form the Grignard reagent of (2,4,5-trifluorophenyl)-magnesium chloride or (2,4,5-trifluorophenyl)-zinc bromide.

10. The method according to claim 5, wherein the compound of formula (e) is produced by:

Step A: reacting a compound of formula (a) in the presence of a base with a benzyl halide to form a compound of formula (b) by an N-substitution reaction,

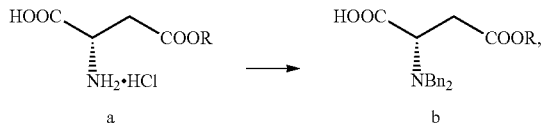

Step B: reacting the compound of formula (b) with a compound of formula (i) in the presence of a base to form the compound of formula (e) by a substitution reaction,

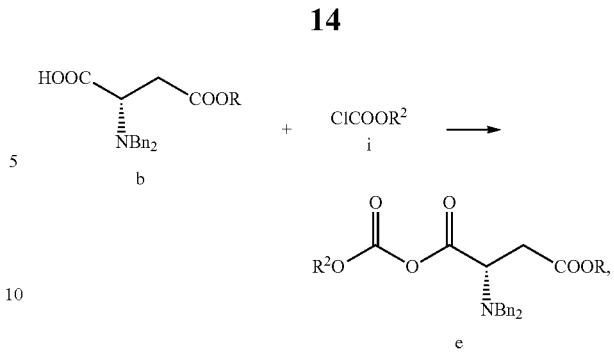

wherein R is a protecting group of carboxyl and, $R^2$ is hydrocarbyl or substituted hydrocarbyl.

11. A method for producing a compound of formula (g) from the compound of formula (f) as defined in claim 1, comprising:

Step E: converting the compound of formula (f) in the presence of a catalyst to a compound of formula (h) by deprotection and carbonyl reduction reaction,

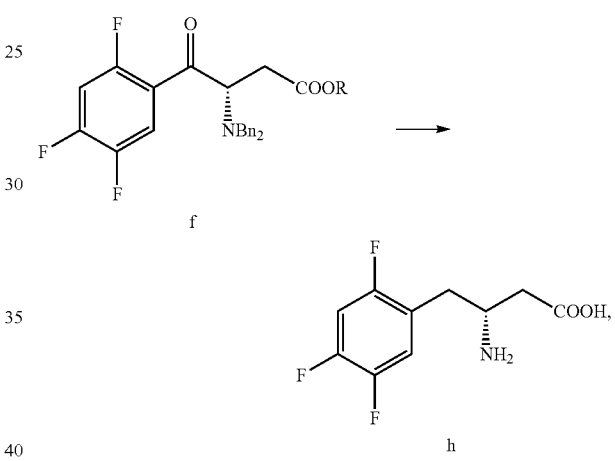

Step F: reacting the compound of formula (h) in the presence of a base with a compound of formula (k) to form the compound of formula (g) by a substitution reaction,

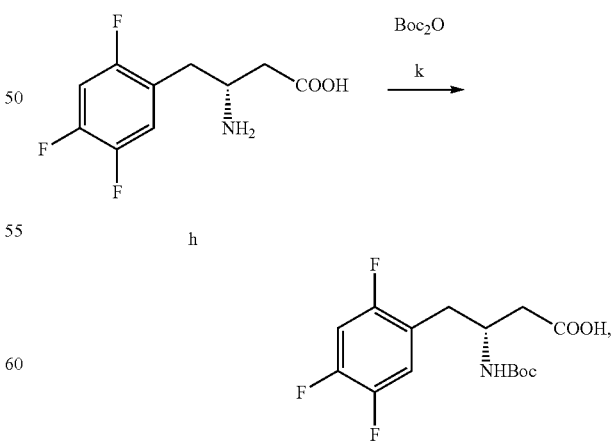

wherein R is a protecting group of carboxyl.

12. The method according to claim 11, wherein the catalyst is Raney Ni or Pd/C.

13. A compound of formula (e) having the following structure,

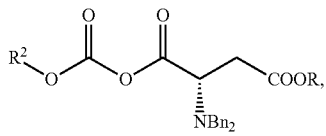

wherein R is a protecting group of carboxyl and, $R^2$ is hydrocarbyl or substituted hydrocarbyl.

14. The compound according to claim 13, wherein, $R^2$ is chain alkyl or substituted chain alkyl, cycloalkyl or substituted cycloalkyl, alkenyl or substituted alkenyl, phenyl or substituted phenyl, benzyl or substituted benzyl.

15. The compound according to claim 14, wherein, $R^2$ is methyl, ethyl, propyl, isopropyl, butyl, isobutyl, tert-butyl, trichloroethyl, 2-chloropropyl, cyclopropyl, cyclopentyl, cyclohexyl, 3-bromocyclohexyl, ethenyl, propenyl, phenyl, p-nitrophenyl, p-chlorophenyl, benzyl, p-nitrobenzyl, or p-chlorobenzyl.

16. The compound according to claim 15, the compound of formula (e) is selected from the group consisting of:
- (S)-2-(dibenzylamino)-4-methoxy-4-oxobutanoic (methyl carbonic) anhydride;
- (S)-2-(dibenzylamino)-4-methoxy-4-oxobutanoic (ethyl carbonic) anhydride;
- (S)-4-(benzyloxy)-2-(dibenzylamino)-4-oxobutanoic (methyl carbonic) anhydride; and
- (S)-4-(benzyloxy)-2-(dibenzylamino)-4-oxobutanoic (ethyl carbonic) anhydride.

17. A method for the preparation of a compound of formula (e), comprising:

Step A: reacting a compound of formula (a) in the presence of a base with a benzyl halide to form a compound of formula (b) by an N-substitution reaction,

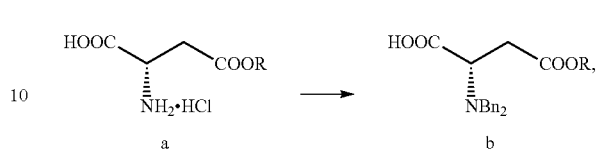

Step B: reacting the compound of formula (b) with a compound of formula (i) in the presence of a base to form a compound of formula (e) by a substitution reaction,

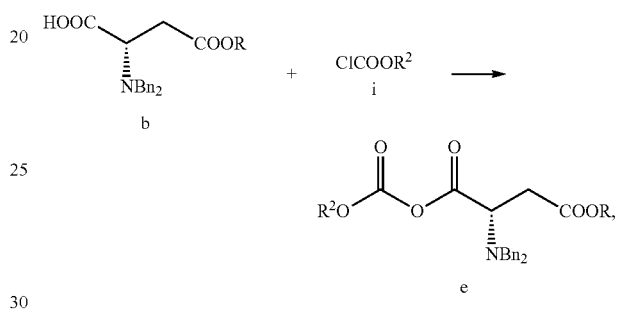

wherein R is a protecting group of carboxyl and, $R^2$ is hydrocarbyl or substituted hydrocarbyl.

* * * * *